United States Patent
Makino et al.

(10) Patent No.: US 6,724,481 B2
(45) Date of Patent: Apr. 20, 2004

(54) GROUND CONTAMINATION DETECTOR

(75) Inventors: Takao Makino, Kanagawa-ken (JP); Masaaki Chiba, Kanagawa-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 232 days.

(21) Appl. No.: 10/099,956

(22) Filed: Mar. 19, 2002

(65) Prior Publication Data

US 2003/0043379 A1 Mar. 6, 2003

(30) Foreign Application Priority Data

Aug. 28, 2001 (JP) .................................. 2001-257896

(51) Int. Cl.$^7$ ............................................. G01N 21/00
(52) U.S. Cl. .............................................. 356/437
(58) Field of Search ............................. 356/432–440, 356/70; 250/243, 339.13; 73/863

(56) References Cited

FOREIGN PATENT DOCUMENTS

JP          8-184553          7/1996

*Primary Examiner*—Michael P. Stafira
*Assistant Examiner*—Amanda Merlino
(74) *Attorney, Agent, or Firm*—Oblon, Spivak, McClelland, Maier & Neustadt, P.C.

(57) ABSTRACT

A ground contamination detector has a duct (21) having an annular opening (21a). The annular opening blows air toward the ground (1) to form an air curtain that defines an enclosed space (2A) between the duct and the ground. The detector also has a pipe (23) having a nozzle that opens in the enclosed space and jets heated air toward the ground, to promote the evaporation of noxious substance (3) and diffuse the evaporated gas in the enclosed space. The detector also has a suction pipe (24) to suck the evaporated gas from the enclosed space and a sensor (25) to analyze the sucked gas. The enclosed space formed by the air curtain defines a detection area on the ground, and the detector collects and analyzes contaminants in the enclosed space in a noncontact way. The detector is installable on a vehicle, to efficiently detect the presence and position of contaminants on the ground in real time.

5 Claims, 7 Drawing Sheets

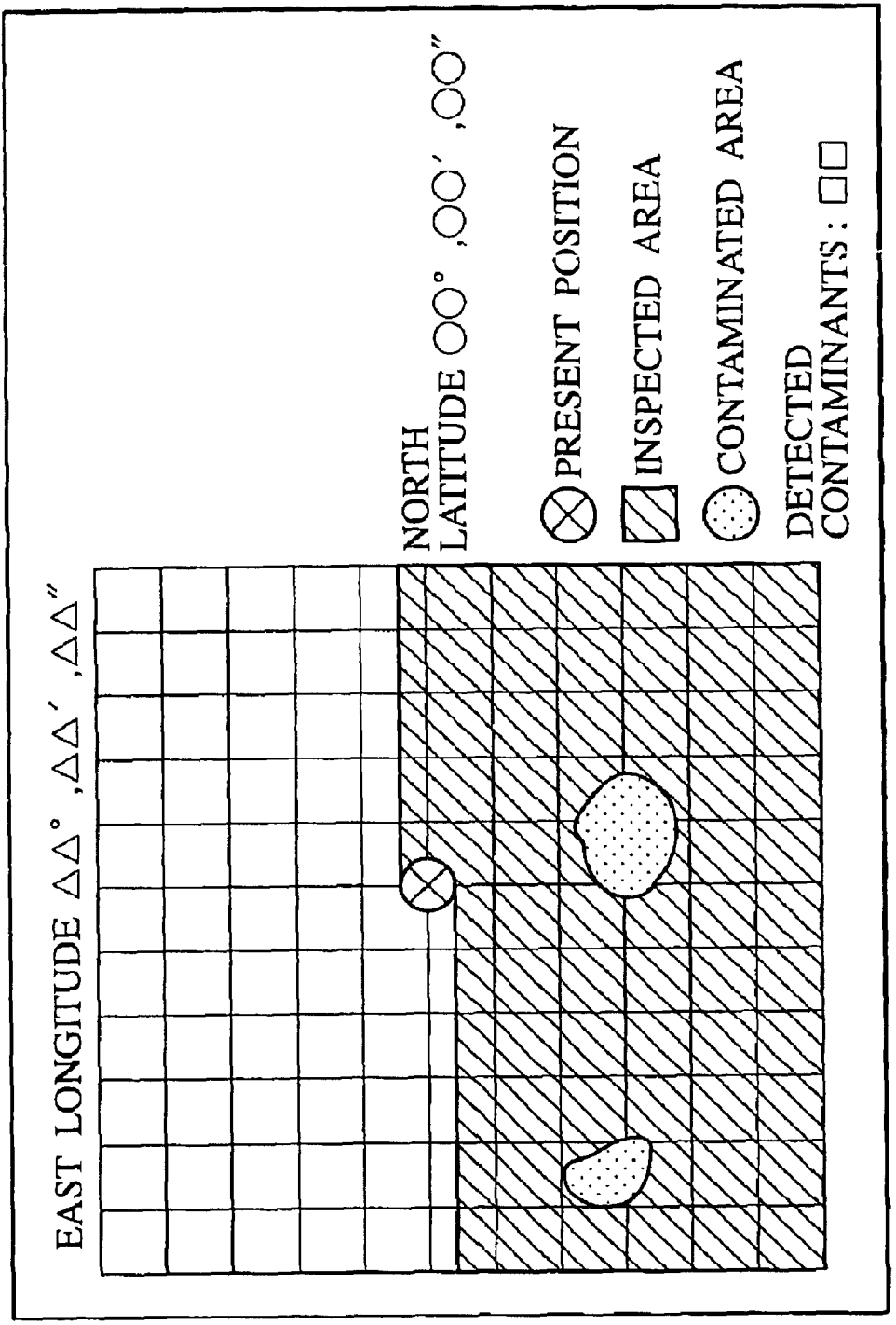

GROUND CONTAMINATION DETECTOR

CROSS REFERENCE TO RELATED APPLICATIONS

This application is based upon and claims the benefit of priority from the prior Japanese Patent Application No. 2001-257896 filed on Aug. 28, 2001, the entire contents of which are incorporated herein by reference.

BACKGROUND OF THE INVENTION

1. Field of the Invention

The present invention relates to a ground contamination detector mounted on, for example, a vehicle to collect elements evaporating from contaminants such as chemical agents (for example, sarin) on the ground, analyze the collected elements with a sensor, and identify the collected elements and a contaminated location on the ground.

2. Description of the Related Art

Detecting noxious contaminants in a wide area on the ground employs a contact detector that directly touches the ground to inspect, or a noncontact detector that does not directly touch the ground to inspect.

An example of the contact detector is a color reaction detector. The color reaction detector employs a detector paper that is wound around a roller and serves as a sensor. The detector paper is brought in contact with the ground and is checked to see if it develops or changes color due to a chemical reaction with substance on the ground, to determine whether or not noxious substance is present on the ground. Another example of the contact detector sets ATR (attenuated total reflection) crystals on the ground, measures the absorption spectra and intensity of infrared rays reflected from the ATR crystals, and determines whether or not noxious substance is present on the ground.

The contact detector must move the detector paper or the ATR crystals along the ground. This is very difficult to achieve if the ground is intricately undulated. The contact detector, therefore, is appropriate only for sampling soil and analyzing the sampled soil for noxious substance. The contact detector is inappropriate for identifying a contaminated location in a wide area on the ground. The contact detector has a risk of exposing the user to a noxious gas evaporating from solid or liquid contaminants on the ground even if the user is not in direct contact with the contaminants.

The noncontact detector does not directly touch solid or liquid contaminants. The noncontact detector detects gaseous elements evaporating from noxious substance, analyzes the detected elements, and determines whether or not there is noxious substance. For example, the noncontact detector emits a laser beam to an object, analyzes a reflected beam from the object, and determines whether or not the object is noxious.

FIGS. 1A, 1B, and 1C show noncontact detectors according to related arts. FIG. 1A shows an FTIR (Fourier transform infrared) gas cell detector. An infrared source A1 emits infrared rays toward a gas cell A2. The gas cell A2 passes a gas in a direction Z. An FTIR sensor A3 measures an absorption spectrum of the gas and detects elements of the gas.

FIG. 1B shows a DIAL (differential absorption lidar) detector. The DIAL detector B1 emits two types of laser beams toward the ground 1, the laser beams being adjusted for an absorption wavelength and a non-absorption wavelength of gas. The laser beams pass through a gas evaporating from noxious substance B2 and are reflected from the ground 1. The DIAL detector B1 measures contrast between the reflected laser beams and determines whether or not there is noxious substance.

FIG. 1C shows a Raman scattering detector. A laser source C1 emits a laser beam toward the ground 1, and sensors C31 to C3$n$ measure the Raman scattering wavelengths $\lambda 1$ to $\lambda n$ of reflected beams from the ground 1. According to the measured wavelengths $\lambda 1$ to $\lambda n$, the Raman scattering detector determines whether or not there is noxious substance.

Unlike the contact detectors, the noncontact detectors are relatively easy to detect a contaminated location in a wide area on the ground. Among the noncontact detectors, the FTIR gas cell detector of FIG. 1A and the DIAL detector of FIG. 1B measure a gas evaporating from noxious substance and floating in a space between the detectors and the ground. For these detectors, it is difficult to identify an exact location on the ground where the noxious substance is present. The reason of this will be explained with reference to FIG. 2.

FIG. 2 is a plan view showing a relationship between a location where noxious substance is present and a location where a gas evaporating from the noxious substance is detected. The noxious substance is at a location A', to produce a noxious gas. The noxious gas drifts due to a wind blowing in a direction Y and scatters over an area B'. Any one of the detectors of the related arts positioned at an observation location C' in the area B' may detect the drifting noxious gas. In this case, the detector is unable to identify the location A' actually contaminated with the noxious substance.

It is known that the Raman scattering detector of FIG. 1C is unable to detect a wet state of the ground, i.e., unable to detect liquid contaminants soaked in the ground. If an object to detect is liquid, the Raman scattering detector requires the object to be a puddle of liquid. Namely, the Raman scattering detector is impractical for detecting noxious substance in a wet state on the ground.

SUMMARY OF THE INVENTION

The present invention provides a ground contamination detector capable of operating on noxious substance in a wet state on the ground, to correctly and speedily detect the noxious substance and a true location thereof on the ground in a noncontact manner.

According to an aspect of the present invention, a ground contamination detector has a space enclosing unit having an annular opening to blow air toward the ground to form an enclosed space on the ground, a suction pipe extending into the enclosed space and having an opening oriented toward the ground to suck a gas from the enclosed space, and a sensor to detect elements of the sucked gas.

According to this aspect, the ground contamination detector forms an enclosed space on the ground to prevent external noxious substance from entering the enclosed space, secures a noncontact state, and identifies a location of the enclosed space on the ground. The suction pipe collects a gas from the enclosed space, and the sensor detects elements of the collected gas. This detector is capable of speedily and correctly identifying a contaminated location on the ground even if the location is in a wet state.

BRIEF DESCRIPTION OF THE DRAWINGS

FIG. 6 shows an example of a screen displayed on a display of the apparatus of FIG. 3;

DETAILED DESCRIPTION OF EMBODIMENTS

Various embodiments of the present invention will be described with reference to the accompanying drawings.

Figure 3:
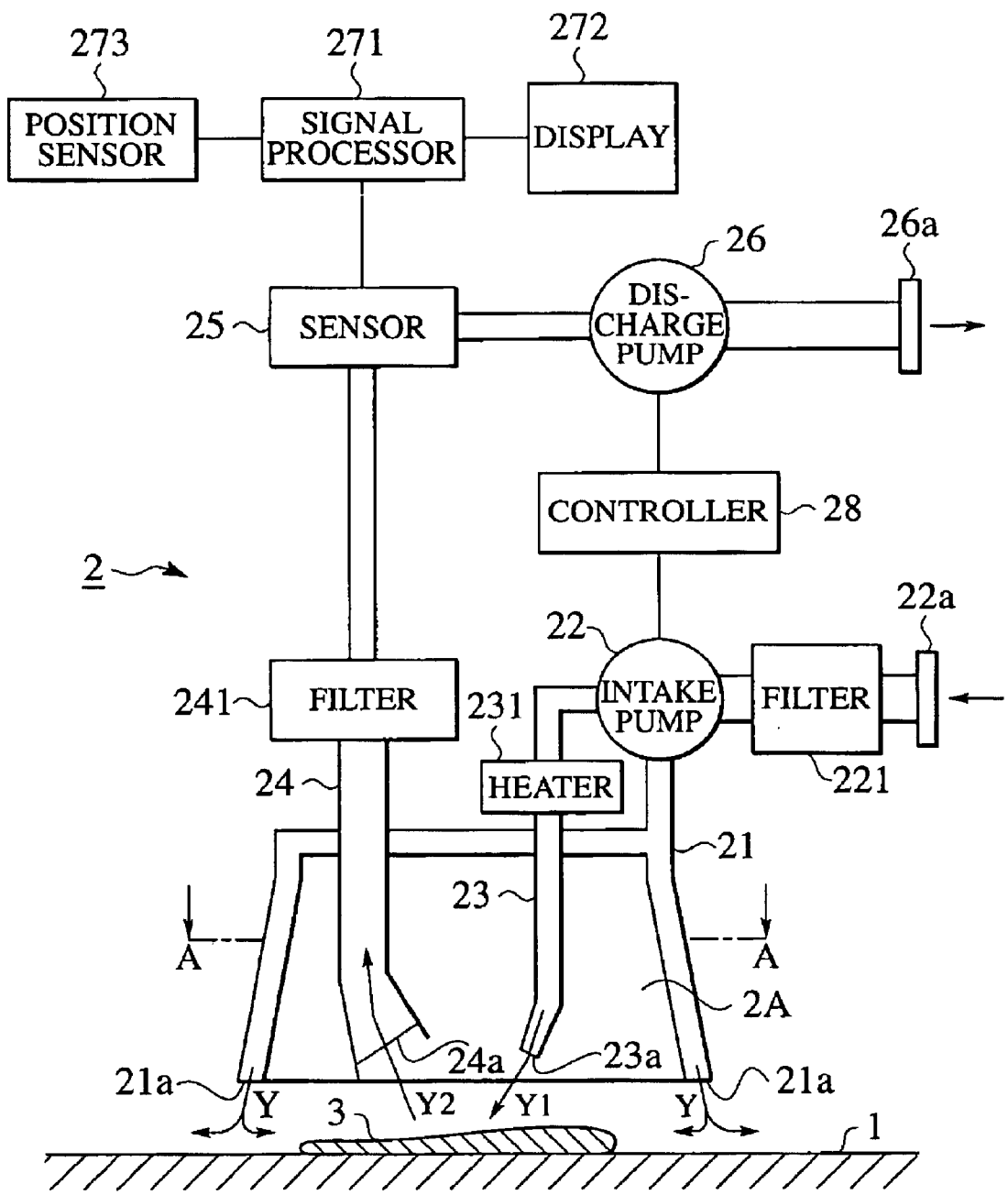
FIG. 3 shows a ground contamination detector according to a first embodiment of the present invention.
Figure 4:
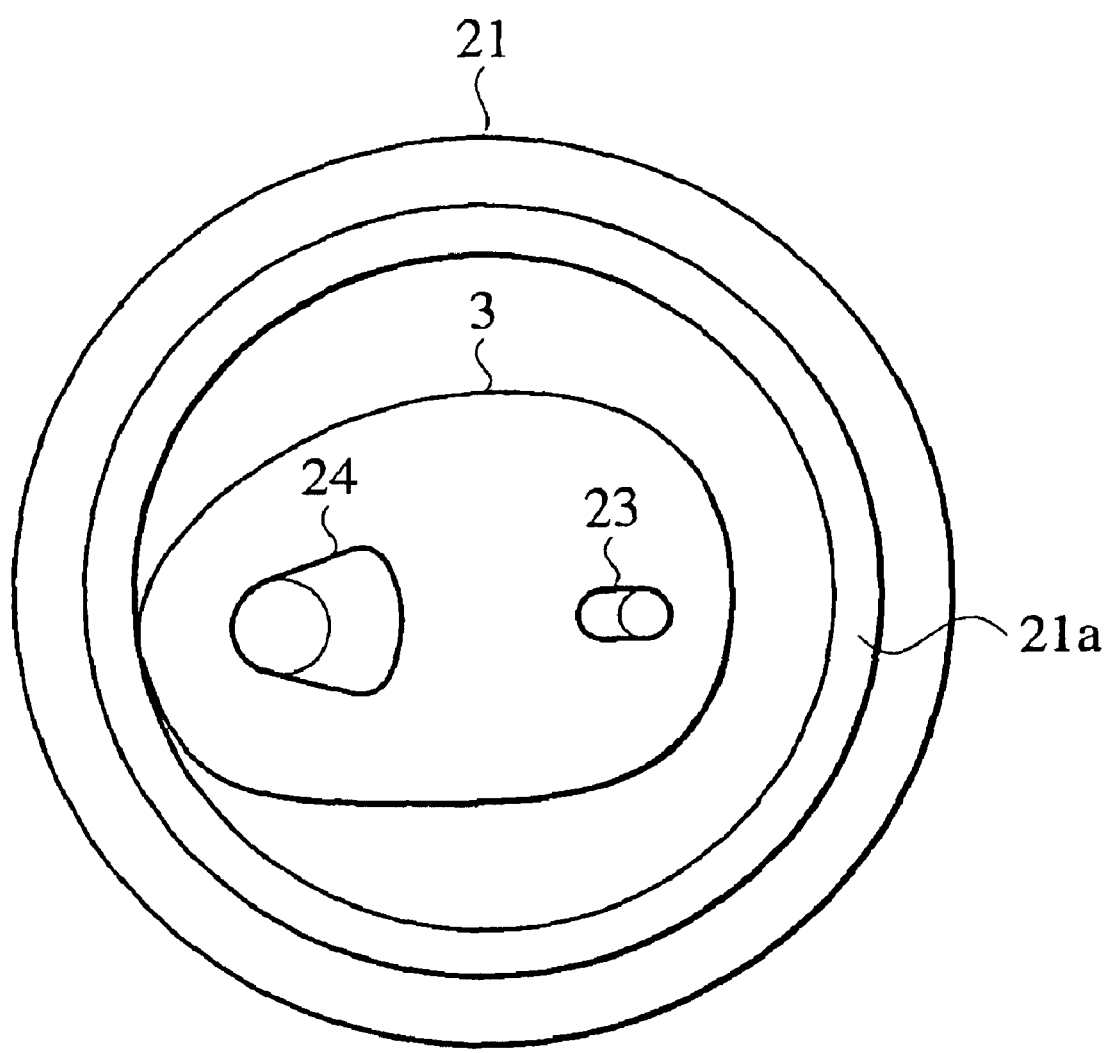
FIG. 4 is a sectional view taken along a line A—A of FIG. 3.

FIG. 3 shows a ground contamination detector according to the first embodiment of the present invention, and FIG. 4 is a sectional view taken along a line A—A of FIG. 3.

The ground contamination detector 2 has a duct 21 having an inverted-tub shape. The duct 21 has an annular opening 21a at a lower end thereof. The opening 21a faces the ground 1 and is oriented outwardly as shown in FIG. 3. An upper end of the duct 21 is connected to an intake pump 22.

The intake pump 22 has an inlet 22a and a filter 221 to draw external air and feed filtered clean air into the duct 21.

The opening 21a of the duct 21 blows air in a direction Y toward the ground 1 to form an air curtain between the opening 21a and the ground 1. The duct 21, the air curtain, and the ground 1 surrounded with the air curtain form an enclosed space 2A.

The intake pump 22 is connected to a pipe 23 extending across the duct 21. The pipe 23 has a nozzle 23a formed at a lower end of the pipe 23. The nozzle 23a opens in the enclosed space 2A, to jet air toward the ground 1. An intermediate part of the pipe 23 is provided with a heater 231 to heat air passing through the pipe 23.

A suction pipe 24 having a relatively large diameter is arranged across the duct 21. The suction pipe 24 has an opening 24a at a lower end thereof. The opening 24a opens in the enclosed space 2A and faces the ground 1.

An upper end of the suction pipe 24 is connected to a filter 241, a sensor 25, and a discharge pump 26. The discharge pump 26 discharges air or gas from the enclosed space 2A to the outside through the suction pipe 24, the filter 241, the sensor 25, and an outlet 26a.

The ground 1 in the enclosed space 2A may involve noxious substance 3, which evaporates and diffuses elements thereof in the enclosed space 2A.

The nozzle 23a of the pipe 23 jets heated air in a direction Y1, to promote the evaporation and diffusion of the noxious substance 3 in the enclosed space 2A and blow the evaporated elements of the noxious substance 3 upwardly. As a result, the opening 24a of the suction pipe 24 efficiently collects a gas containing the evaporated elements in a direction Y2.

The collected gas is passed through the filter 241 to remove unwanted materials such as earth, sand, dust, and liquid that may hinder the detecting and analyzing operations of the sensor 25.

Figure 1A:
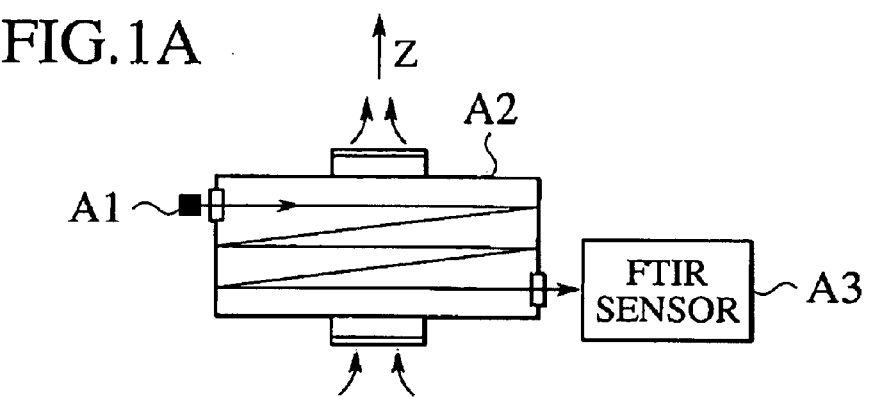
FIGS. 1A to 1C show ground contamination detectors according to related arts.
Figure 1B:
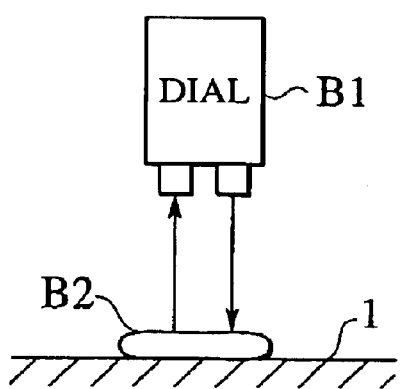
Figure 1C:
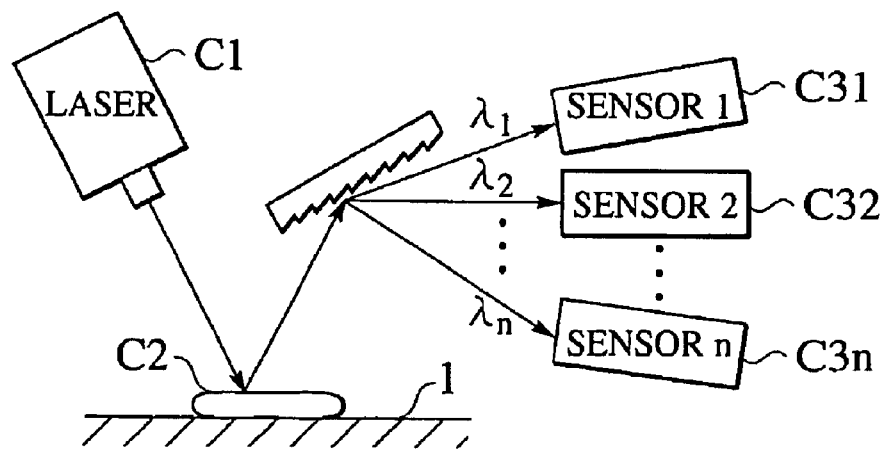
Figure 2:
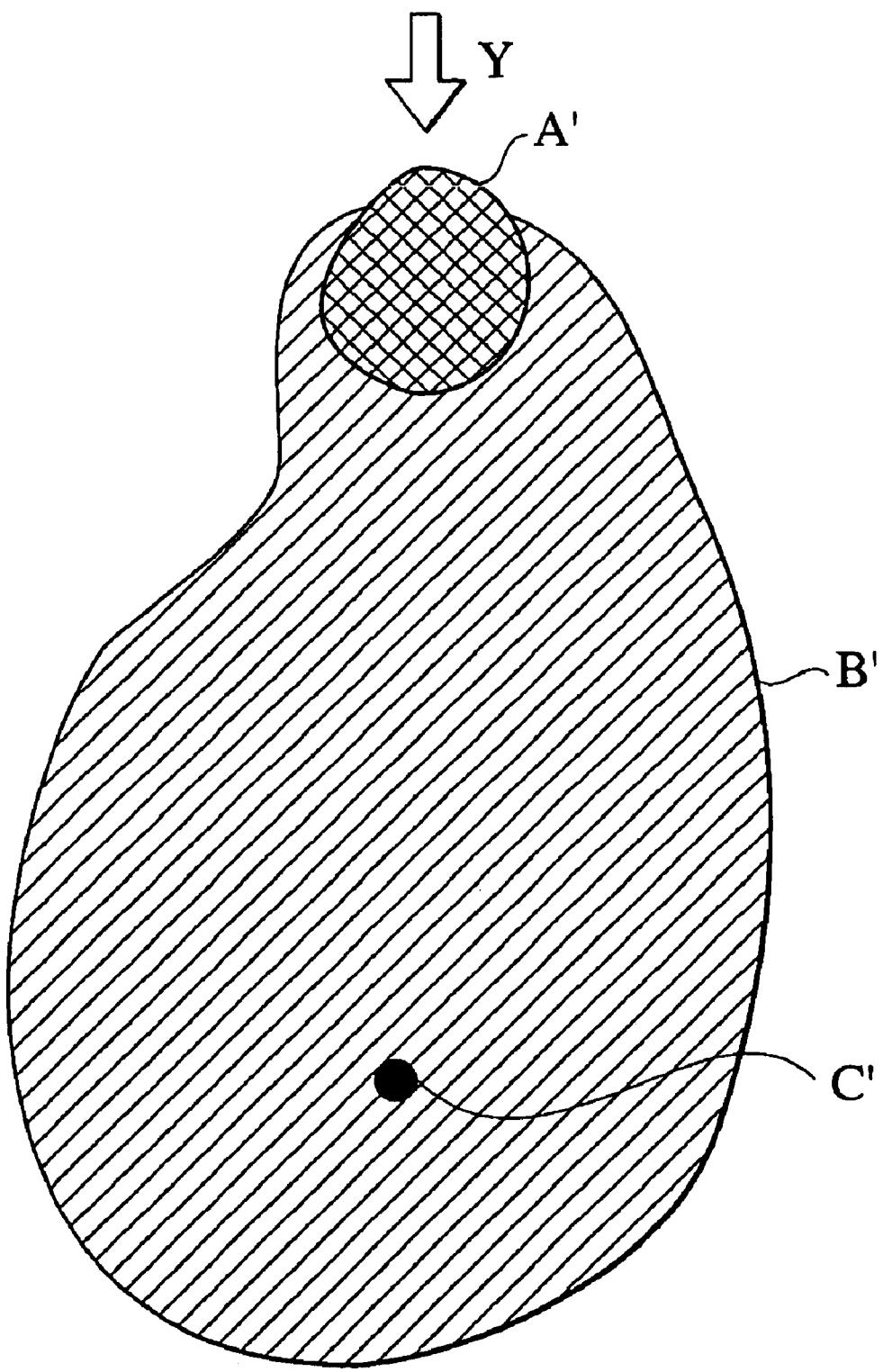
FIG. 2 is a plan view showing a relationship between a location where noxious substance is present and a location where a gas evaporating from the noxious substance is detected according to the related arts.

The sensor 25 may employ the FTIR spectrometer of FIG. 1A to carry out an infrared absorption spectrum analysis to detect the elements of the noxious substance 3 contained in the collected gas.

After the sensor 25, the gas is discharged to the outside through the discharge pump 26 and outlet 26a.

The analysis carried out by the sensor 25 provides, for example, the elements of the noxious substance 3 and the quantities of the elements. The analyzed result is passed through a signal processor 271 and is displayed on a display 272.

The signal processor 271 is connected to a position sensor 273, which measures a geographical position on the ground 1 where the suction pipe 24 has collected the gas and transfers the measured position to the signal processor 271.

The signal processor 271 combines the analyzed result from the sensor 25 and the measured position from the position sensor 273 and supplies the combined data to the display 272. The display 272 displays the elements of the noxious substance 3, the quantities of the elements, and the position on the ground 1 where the elements have been detected.

A controller 28 controls an intake quantity of the intake pump 22 and a discharge quantity of the discharge pump 26, so that an air pressure in the enclosed space 2A is always higher than an atmospheric pressure.

Due to the higher pressure in the enclosed space 2A and the blocking function of the air curtain produced by the duct 21, no external air enters or contaminates the enclosed space 2A. The ground contamination detector 2, therefore, is capable of collecting contaminants (gaseous elements) only from the enclosed space 2A.

Figure 5:
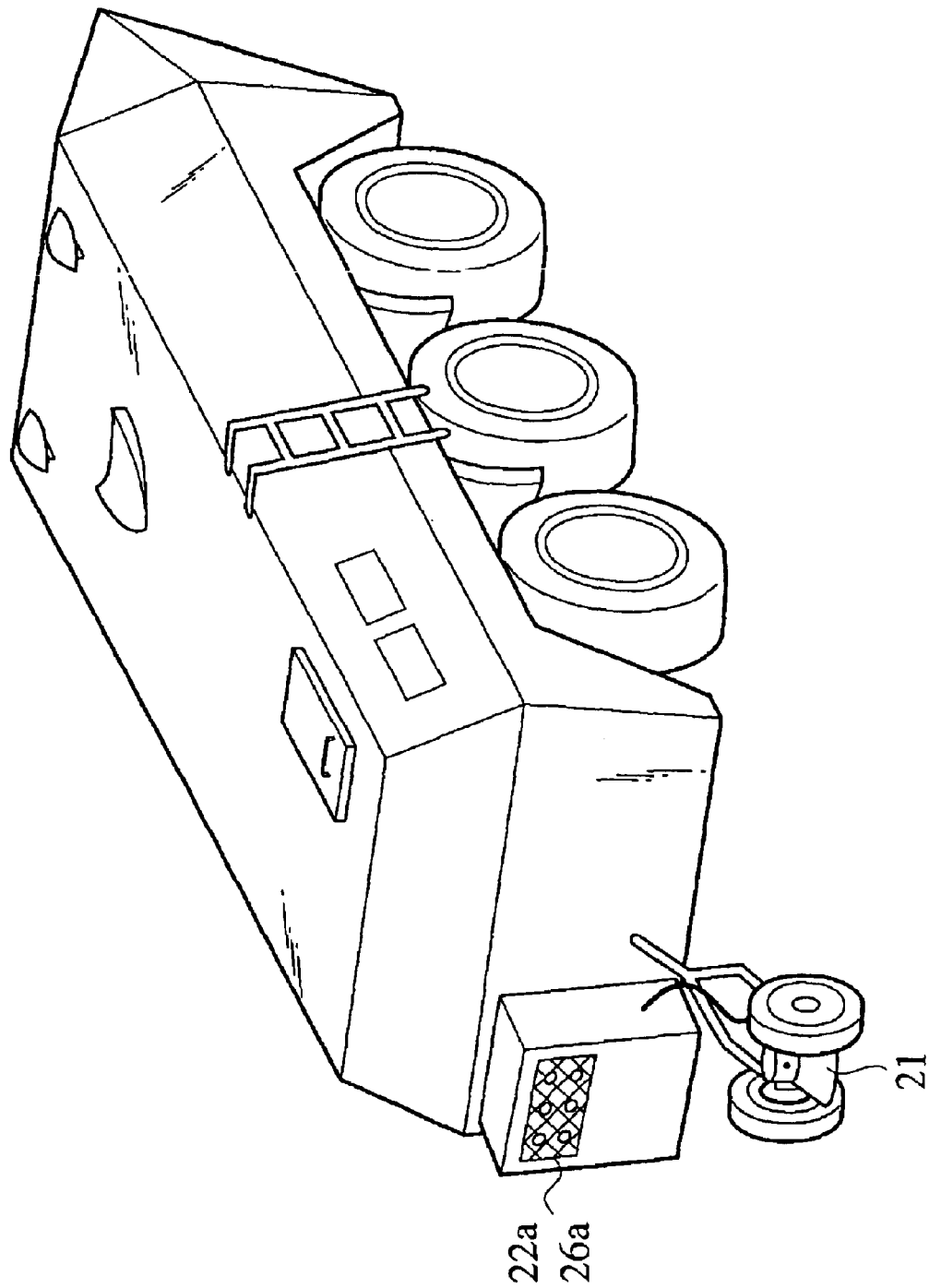
FIG. 5 is a perspective view showing a vehicle on which the apparatus of FIG. 3 is installable.

FIG. 5 shows a vehicle on which the ground contamination detector 2 of the embodiment is installable. The detector 2 is capable of detecting ground contamination in a non-contact way, and therefore, is installable on the vehicle of FIG. 5. In this case, the duct 21 to produce the enclosed space 2A, the inlet 22a of the intake pump 22, and the outlet 26a of the discharge pump 26 may be arranged at the rear of the vehicle.

The vehicle with the detector 2 may be manned or unmanned. If the vehicle is unmanned, it will remotely be controlled to automatically carry out a contamination detecting operation.

When the detector 2 is installed on a vehicle, the position sensor 273 may be a GPS (global positioning system) to accurately display a detecting location on the display 272.

FIG. 6 shows an example of a screen displayed on the display 272 of the apparatus 2 of FIG. 3. In FIG. 6, the display 272 displays a map of the area to be searched for noxious substance, the present location of the detector 2, contaminated locations detected, and detected contaminants. The display 272 may display information not in real time. For example, data detected by the detector 2 may be accumulated in a storage medium such as a magnetic disk or an optical disk, and after completing a detecting operation for a predetermined area on the ground, the accumulated data may be displayed on the display 272 or printed on a sheet of paper.

According to the first embodiment, the pipes 23 and 24 are separated from each other in the enclosed space 2A. This does not limit the present invention. The pipes 23 and 24 may optionally be arranged in the enclosed space 2A if the pipe 23 properly jets heated air to blow and diffuse elements evaporating from noxious substance into the enclosed space 2A and if the pipe 24 efficiently collects the diffused elements.

Figure 7A:
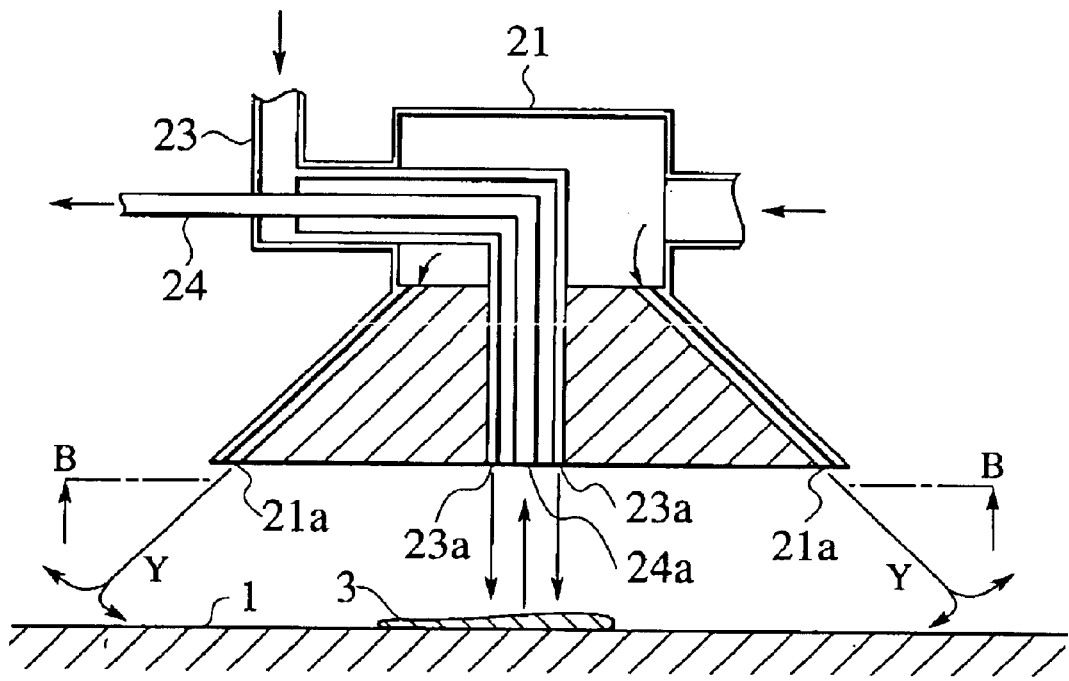
FIG. 7A partly shows a ground contamination detector according to a second embodiment of the present invention.
Figure 7B:
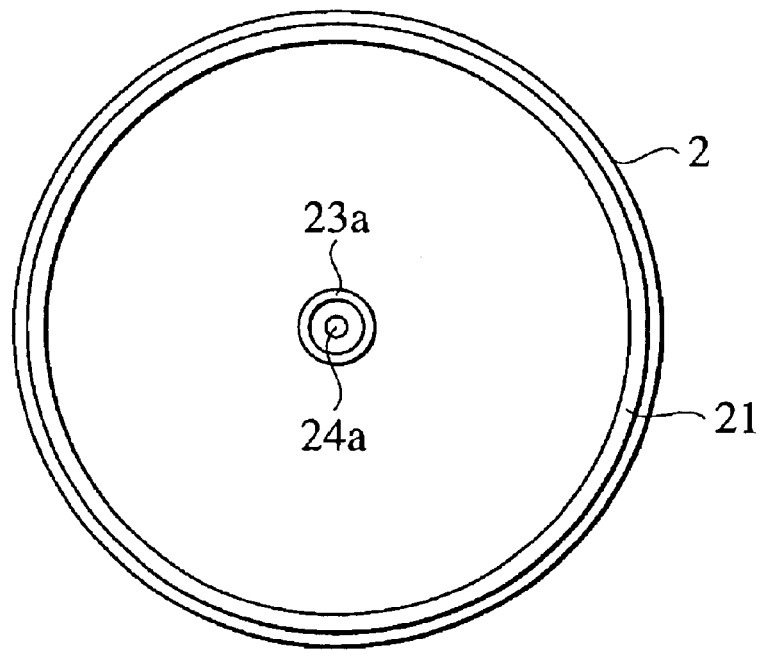
FIG. 7B is a bottom view along a line B—B of FIG. 7A.

FIGS. 7A and 7B partly show a ground contamination detector according to the second embodiment of the present invention. The second embodiment employs pipes 23 and 24 that are concentrically arranged. The other parts of the second embodiment are substantially the same as those of the first embodiment.

FIG. 7A shows only a different part of the second embodiment from the first embodiment. FIG. 7B is a bottom view along a line B—B of FIG. 7A.

The ground contamination detector of the second embodiment has a duct 21 with a conical hollow base. This base is provided with an annular opening 21a whose orientation is more outward than the opening 21a of the first embodiment.

According to the second embodiment, the opening 21a blows air in a direction Y toward the ground 1, to form an air curtain. The duct 21, the air curtain, and the ground 1 surrounded with the air curtain form an enclosed space 2A.

At the center of the duct 21, an opening 24a of the suction pipe 24 is open in the enclosed space 2A toward the ground 1. Concentrically around the suction pipe 24, the pipe 23 is arranged with an annular nozzle 23a of the pipe 23 opening in the enclosed space 2A toward the ground 1.

The annular nozzle 23a jets heated air to blow elements evaporating from noxious substance 3 toward the opening 24a of the suction pipe 24. As a result, the suction pipe 24 efficiently collects the evaporated elements.

In each of the embodiments mentioned above, the duct 21 has an annular shape. This does not limit the present invention. The duct 21 may have an optional shape such as a rectangular pipe shape, if it can properly form an air curtain to enclose a space. According to the present invention, the pipes 23 and 24 may have optional diameters and shapes.

In each of the embodiments, the duct 21 has an annular opening. The opening of the duct 21 may have an optional configuration, if it can properly form an air curtain to enclose a space. For example, the opening of the duct 21 may be made of small nozzles annularly arranged at regular intervals.

As explained above, the ground contamination detector according to the present invention is capable of quickly and correctly detecting, in a noncontact way, noxious substance in a specified area on the ground even if the noxious substance is in a wet state on the ground. This detector is installable on a vehicle, to provide practical advantages.

The ground contamination detector according to the present invention forms an air curtain to enclose a space on the ground and correctly detects contaminants in the enclosed space in a noncontact way. This detector is installable on a vehicle, to serve for detecting and removing contaminants on the ground.

Additional advantages and modifications of the present invention will readily occur to those skilled in the art. Therefore, the present invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A ground contamination detector comprising:
   a space enclosing unit having an annular opening to blow air toward the ground to form an enclosed space on the ground;
   a suction pipe extending into the enclosed space and having an opening oriented toward the ground to suck a gas from the enclosed space; and
   a sensor to detect elements of the sucked gas.

2. The ground contamination detector of claim 1, further comprising:
   a display to display a detection result provided by the sensor.

3. The ground contamination detector of any one of claims 1, further comprising:
   a blower unit having a nozzle to blow air toward the ground in the enclosed space.

4. The ground contamination detector of claim 3, wherein:
   the blower unit is provided with a heater to blow hot air from the nozzle toward the ground in the enclosed space.

5. The ground contamination detector of any one of claims 2, wherein:
   the display displays geographical and positional information about the enclosed space in combination with the detection result.

* * * * *